United States Patent
Song et al.

(10) Patent No.: US 12,426,873 B2
(45) Date of Patent: Sep. 30, 2025

(54) ENDOSCOPIC SUTURING DEVICE

(71) Applicant: KOREA UNIVERSITY RESEARCH AND BUSINESS FOUNDATION, Seoul (KR)

(72) Inventors: Yongnam Song, Seoul (KR); Yoonjin Kim, Seoul (KR); Dokwan Lee, Seoul (KR); Daehie Hong, Seoul (KR); Hoon Jai Chun, Seoul (KR); Bora Keum, Seoul (KR); Hyuk Soon Choi, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 276 days.

(21) Appl. No.: 17/925,103

(22) PCT Filed: May 12, 2021

(86) PCT No.: PCT/KR2021/005923
§ 371 (c)(1),
(2) Date: Nov. 14, 2022

(87) PCT Pub. No.: WO2021/230643
PCT Pub. Date: Nov. 18, 2021

(65) Prior Publication Data
US 2023/0225723 A1    Jul. 20, 2023

(30) Foreign Application Priority Data
May 13, 2020   (KR) .................. 10-2020-0057030

(51) Int. Cl.
*A61B 17/04* (2006.01)
*A61B 17/06* (2006.01)
*A61B 90/00* (2016.01)

(52) U.S. Cl.
CPC .... *A61B 17/0469* (2013.01); *A61B 17/06066* (2013.01); *A61B 2090/034* (2016.02)

(58) Field of Classification Search
CPC .......... A61B 17/0469; A61B 17/06066; A61B 2090/034; A61B 2017/00296; A61B 2017/0608; A61B 17/0482; A61B 17/062
See application file for complete search history.

(56) References Cited

U.S. PATENT DOCUMENTS

2006/0224184 A1* 10/2006 Stefanchik ......... A61B 17/0482
606/222
2006/0282093 A1   12/2006 Shelton, IV et al.
(Continued)

FOREIGN PATENT DOCUMENTS

JP           4340043 B2    10/2009
JP       2015-171581 A    10/2015
(Continued)

OTHER PUBLICATIONS

International Search Report issued on Sep. 6, 2021, in corresponding PCT/KR2021/005923 (8 pages in Korean).
(Continued)

*Primary Examiner* — Sarah A Long
*Assistant Examiner* — James R Mcginnity
(74) *Attorney, Agent, or Firm* — NSIP Law (57) ABSTRACT

The present invention relates to an endoscope suturing device and, more specifically, to an endoscopic suturing device capable of suturing a range of incisions by using an endoscope. According to the present invention, a wide range of incisions can be continuously sutured with high suturing power by using an endoscope, the suturing procedure time can be shortened, and a suturing method using a suture can minimize leftover foreign substances in the body, and thus can prevent side effects caused by the foreign substances. In (Continued)

addition, by using an endoscope, suturing with high-reliability is possible regardless of the range of suture areas, and thus the present invention can be used for simple suturing procedures and various internal surgeries such as gastrointestinal reduction surgery and NOTES, which uses a natural orifice.

19 Claims, 9 Drawing Sheets

(56) References Cited

U.S. PATENT DOCUMENTS

| | | | | |
|---|---|---|---|---|
| 2007/0239175 | A1* | 10/2007 | Stokes | A61B 17/1114 |
| | | | | 606/144 |
| 2010/0004663 | A1 | 1/2010 | Murphy et al. | |
| 2014/0172015 | A1* | 6/2014 | Martin | A61B 17/06114 |
| | | | | 606/223 |
| 2015/0112134 | A1* | 4/2015 | Suehara | A61B 1/0052 |
| | | | | 600/109 |
| 2019/0029668 | A1* | 1/2019 | Meade | A61B 17/0491 |
| 2019/0388088 | A1* | 12/2019 | Deck | A61B 17/0483 |
| 2021/0177399 | A1* | 6/2021 | Rastoga | A61B 34/70 |

FOREIGN PATENT DOCUMENTS

| | | |
|---|---|---|
| JP | 2015-231572 A | 12/2015 |
| KR | 10-2009-0027188 A | 3/2009 |
| KR | 10-16570331 B1 | 9/2016 |

OTHER PUBLICATIONS

Korean Decision of Grant a Patent issued on Apr. 28, 2022, in corresponding Korean Patent Application No. 10-2020-0057030 (3 pages in Korean).

* cited by examiner

ENDOSCOPIC SUTURING DEVICE

CROSS REFERENCE TO RELATED APPLICATIONS

This application is a U.S. National Stage Application of International Application No. PCT/KR2021/005923, filed on May 12, 2021, which claims the benefit under 35 USC 119 (a) and 365 (b) of Korean Patent Application No. 10-2020-0057030 filed on May 13, 2020 in the Korean Intellectual Property Office, the entire disclosures of which is incorporated herein by reference for all purposes.

TECHNICAL FIELD

The present invention relates to an endoscopic suturing device, and more particularly to an endoscopic suturing device capable of suturing an incision using an endoscope.

BACKGROUND ART

In general, incision and suturing procedures are performed for access to a sub-tissue, an organ, a joint, a skeleton, etc. in the medical field. Meanwhile, when gastrointestinal ulcer or perforation occurs, a suturing procedure is performed using a medical clip capable of being mounted to an endoscope.

When the medical clip is used, however, a large number of clips are necessary to suture a wide range of tissue due to a narrow suturing range and low suturing reliability, and continuous suturing is not possible, whereby suturing time is increased.

In addition, the medical clip used for suturing remains in the body as foreign matter, whereby a tumor may occur.

(Patent Document 1) Korean Patent Application Publication No. 10-2009-0027188 (published on Mar. 16, 2009)

DISCLOSURE

Technical Problem

Therefore, it is an object of the present invention to provide an endoscopic suturing device capable of continuously suturing a wide incision range with high suturing force using an endoscope.

It is another object of the present invention to provide an endoscopic suturing device capable of minimizing residual foreign matter in the body by suturing using a suture.

Technical Solution

In an aspect, the present invention provides an endoscopic suturing device including a body member having formed thereon a coupling portion configured to allow an endoscope to be coupled thereto, a curved needle configured to allow a suture to be coupled thereto, the curved needle being rotatably seated on the body member, a needle driver brought into contact with the curved needle, the needle driver being configured to rotate the curved needle, a driven link configured to allow the needle driver to be coupled thereto, the driven link being configured to be rotatable, a driving link spaced apart from the driven link, the driving link being configured to be rotatable, a connection link configured to connect the driving link and the driven link to each other and to transmit rotational force of the driving link to the driven link, and a power supply source coupled to the driving link, the power supply source being configured to provide rotational force to the driving link.

The body member may be provided with a projecting portion, the connection link may be provided with a through-hole, and the projecting portion may be inserted through the through-hole of the connection link and the connection link may be moved in the state in which at least a part of an inner circumference of the through-hole is in contact with the projecting portion, wherein the through-hole may be configured such that the width of the through-hole is gradually changed from a central part to opposite ends thereof.

The through-hole may be configured such that the shape of the through-hole from the central part to a first end, which is one end, and the shape of the through-hole from the central part to a second end, which is the other end, are symmetrical to each other.

The through-hole may be formed such that the width of the through-hole is increased from the central part to a predetermined first part extending toward the first end and the width of the through-hole is decreased from the first part to the first end.

In addition, the through-hole may be formed such that the width of the through-hole is increased from the central part to a predetermined second part extending toward the second end and the width of the through-hole is decreased from the second part to the second end.

The through-hole may be curved.

The power supply source may include a wire wound around the driving link, the wire having two ends, a handle coupled to one of the ends of the wire, the handle being configured to pull the wire, and an elastic member connected to the other of the ends of the wire, the elastic member being configured to provide elastic force to the wire, the body member may be provided with a wire supporting portion configured to support the wire, and the wire may be wound around the driving link, wherein the wire may be configured to have an intersection that intersects between the driving link and the wire supporting portion.

When the wire is pulled by operation of the handle, the driving link may be rotated in any one of a clockwise direction and a counterclockwise direction, whereby the elastic member may be elastically contracted, and when power pulling the wire is removed, the elastic member may be elastically expanded by elastic restoring force of the elastic member, whereby the driving link may be rotated in a direction opposite the rotation direction when the wire is pulled.

The elastic member may include a spring configured to allow the wire to be disposed therein and a compression portion coupled to an end of the spring and to the wire, wherein the compression portion may be configured to compress the spring when the wire is pulled.

The needle driver may be coupled to the driven link and may be formed so as to project from the driven link to the curved needle, and the curved needle may be provided with a driver recess configured to allow the needle driver to be brought into contact therewith.

In addition, the needle driver may be formed so as to be gradually inclined from the front to the rear in an advance direction of the needle driver.

In addition, the needle driver may include a first straight portion projecting in a straight line from a front of the driven link in the advance direction of the needle driver, a second straight portion projecting in a straight line from a rear of the driven link in the advance direction of the needle driver, the second straight portion having a smaller length than the first straight portion, and a first inclined portion configured to connect the first straight portion and the second straight portion to each other in an inclined state.

The driver recess may be provided with a second inclined portion corresponding to the first inclined portion of the needle driver such that the needle driver is seated in the driver recess.

In addition, the driver recess may be provided in a pair, the pair of driver recesses may be formed in the curved needle at positions at which the driver recesses face each other, and the second inclined portions of the pair of driver recesses may be formed so as to be inclined in opposite directions.

The endoscopic suturing device may further include a needle stopper disposed at a position opposite the needle driver, wherein the needle stopper may be brought into contact with the curved needle to stop the curved needle.

The needle stopper may include a supporting rod coupled to the body member and a pair of projecting portions projecting from the supporting rod to the curved needle, and the curved needle may be provided with a stopper recess configured to allow the projecting portions to be brought into contact therewith.

Each of the projecting portions may be formed so as to be gradually inclined from the front to the rear in the advance direction of the curved needle.

Each of the projecting portions may include a third straight portion projecting in a straight line from a front of the supporting rod in the advance direction of the curved needle, a fourth straight portion projecting in a straight line from a rear of the supporting rod in the advance direction of the curved needle, the fourth straight portion having a smaller length than the third straight portion, and a third inclined portion configured to connect the third straight portion and the fourth straight portion to each other in an inclined state.

The stopper recess may be provided with a fourth inclined portion corresponding to the third inclined portion of each of the projecting portions such that each of the projecting portions of the needle stopper is seated in the stopper recess.

The pair of projecting portions may be disposed at opposite positions, and the third inclined portions of the pair of projecting portions may be formed so as to be inclined in opposite directions.

Advantageous Effects

Therefore, embodiments of the present invention have an effect in that it is possible to continuously suture a wide incision range with high suturing force using an endoscope.

In addition, the embodiments of the present invention have an effect in that it is possible to shorten suturing time.

In addition, the embodiments of the present invention have an effect in that it is possible to minimize residual foreign matter in the body by suturing using a suture, thereby preventing side effects due to the foreign matter.

In addition, the embodiments of the present invention have an effect in that it is possible to perform suturing with high reliability irrespective of a suture range using an endoscope, and therefore the present invention can be usefully used for simple suturing procedures and various internal surgeries such as gastrointestinal reduction surgery and NOTES, which uses a natural opening.

BEST MODE

Hereinafter, preferred embodiments of the present invention will be described in detail with reference to the accompanying drawings. It should be noted that terms or words used in this specification and the claims are not to be interpreted as having ordinary and dictionary-based meanings but as having meanings and concepts coinciding with the technical idea of the present invention based on the principle that the inventors may properly define the concepts of the terms in order to explain the invention in the best method. Accordingly, embodiments described in this specification and constructions shown in the drawings are merely the most preferred embodiments of the present invention and do not speak for the entirety of the technical idea of the present invention, and therefore it should be understood that various replaceable equivalents and modifications may be possible at the time of filing the present application.

In the accompanying drawings, the size of each element or a specific portion constituting the element is exaggerated, omitted, or schematically illustrated for convenience of description and clarity. Therefore, the size of each element does not entirely reflect the actual size thereof. A detailed description of related known functions and configurations will be omitted when the same may obscure the subject matter of the present invention.

The term "coupled" or "connected" used in this specification involves the case in which one member is indirectly coupled or indirectly connected to another member via a joint member as well as the case in which one member is directly coupled or directly connected to another member.

Figure 1:
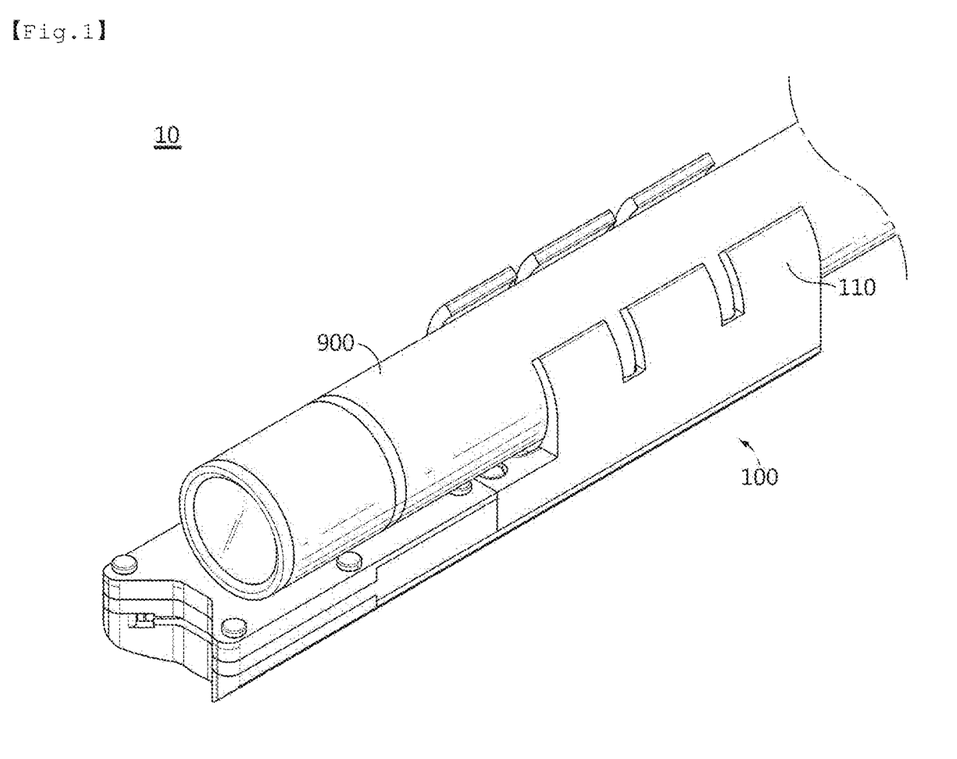
FIG. 1 is a perspective view of an endoscopic suturing device according to an embodiment of the present invention to which an endoscope is coupled.
Figure 2:
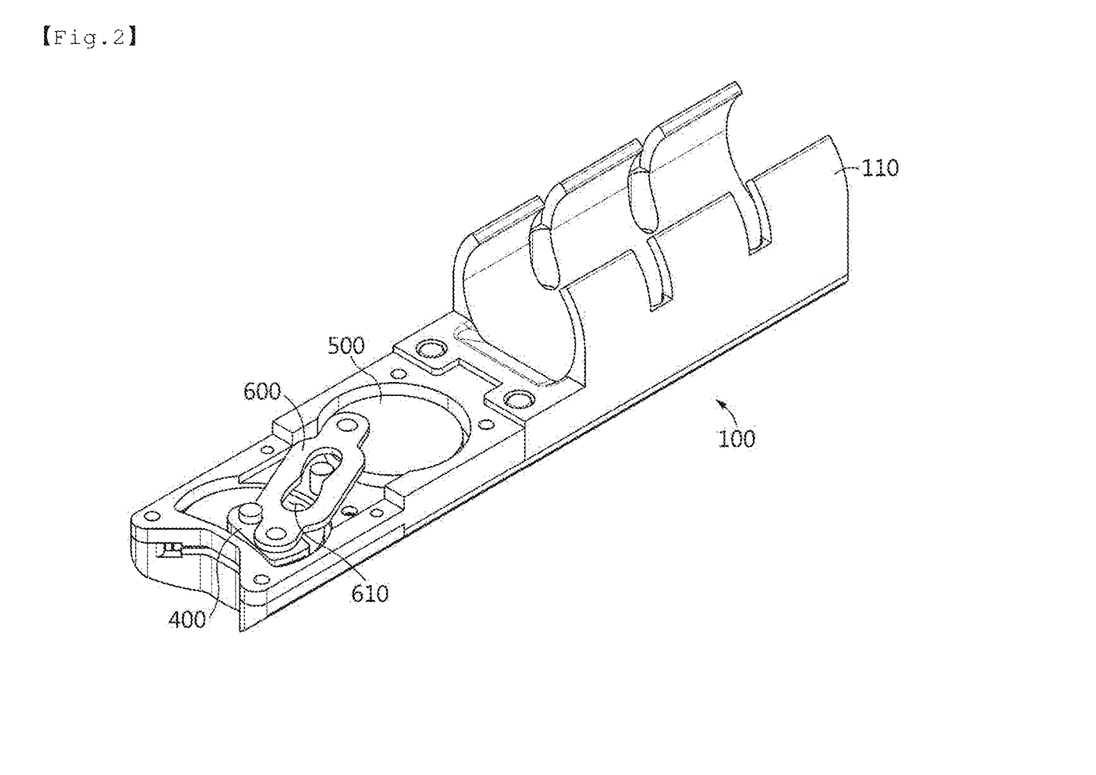
FIG. 2 is a partial exploded view of the endoscopic suturing device according to the embodiment of the present invention.
Figure 3:
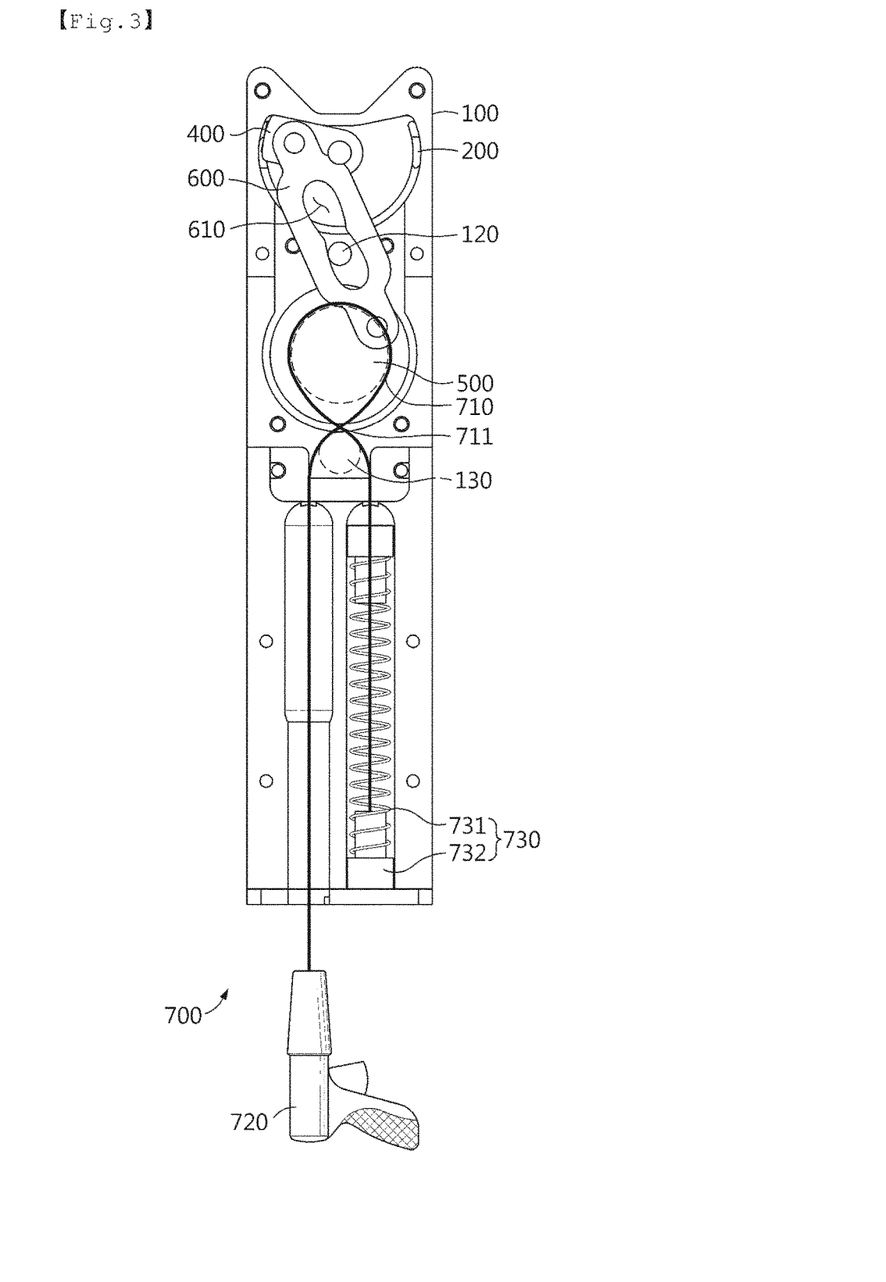
FIGS. 3 and 4 are sectional views illustrating the principle by which the endoscopic suturing device according to the embodiment of the present invention is operated.
Figure 4:
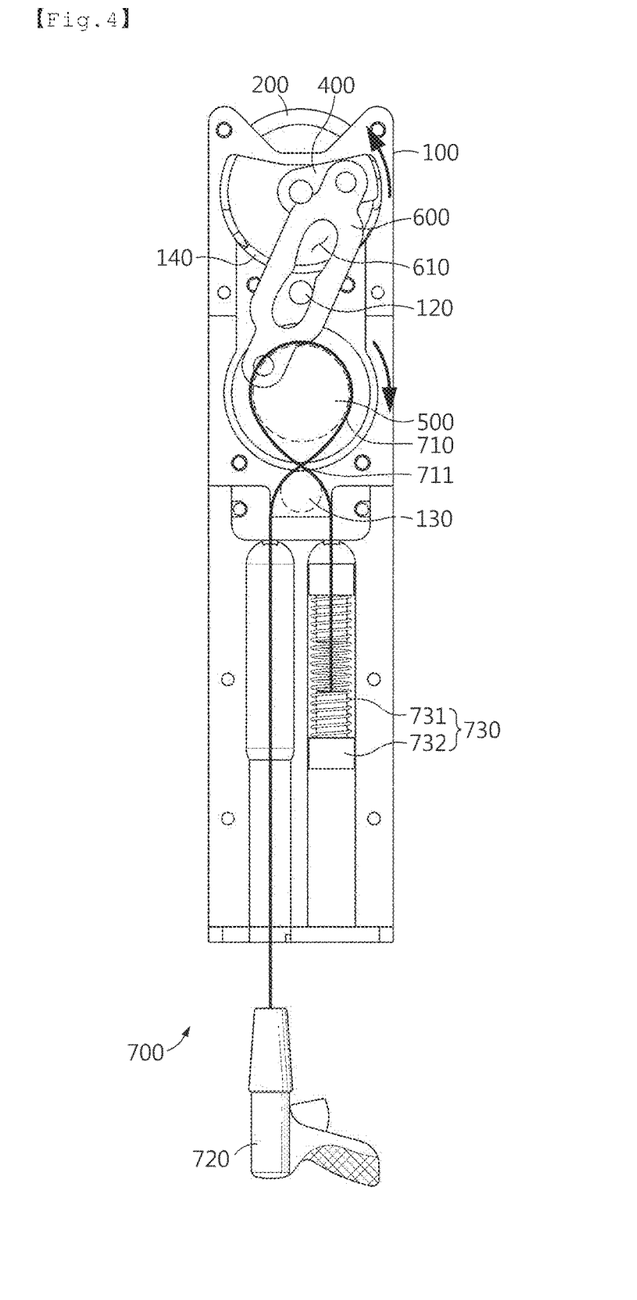
Figure 5:
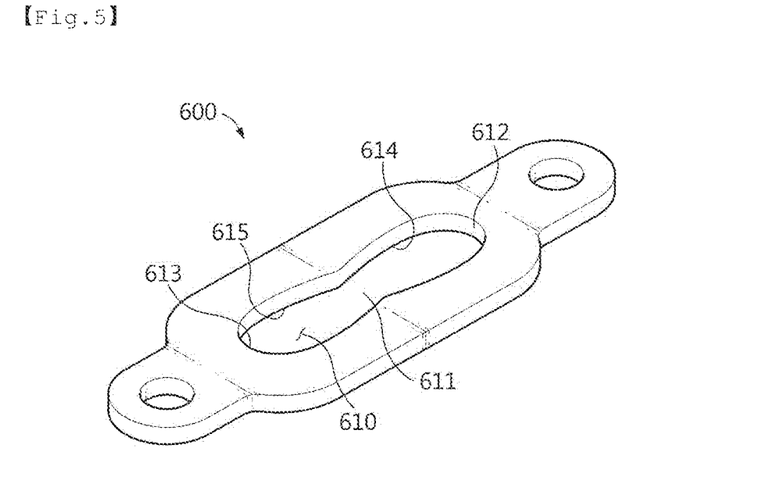
FIG. 5 is a view showing a connection link in the endoscopic suturing device according to the embodiment of the present invention.
Figure 6:
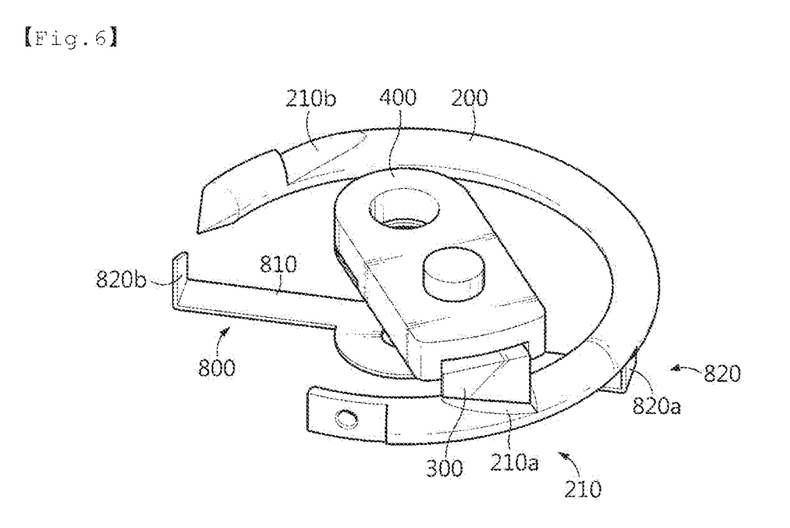
FIG. 6 is a perspective view showing the state in which a needle driver and a needle stopper are in contact with a curved needle in the endoscopic suturing device according to the embodiment of the present invention.
Figure 7:
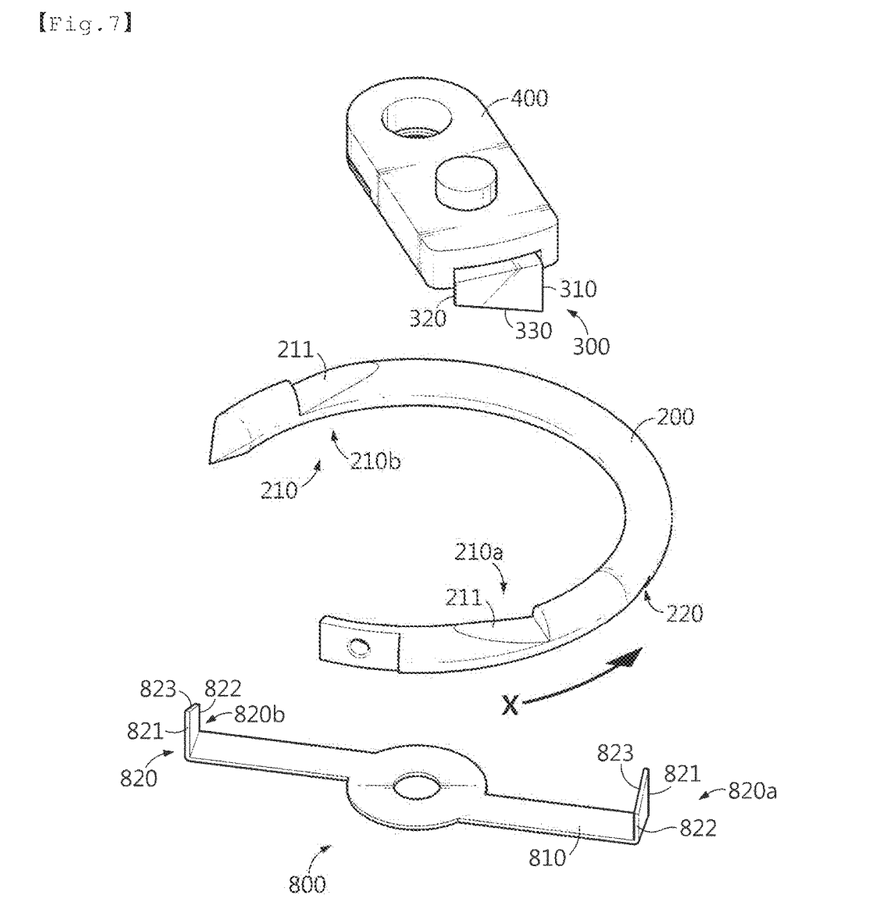
FIG. 7 is a perspective view showing the state in which the needle driver and the needle stopper are separated from the curved needle of FIG. 6.
Figure 8:
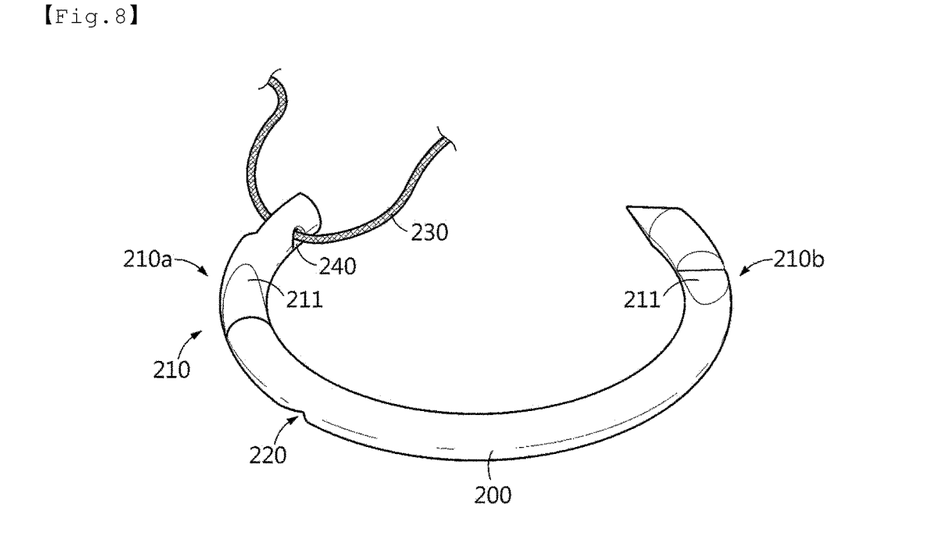
FIG. 8 is a perspective view of an upper side of the curved needle in the endoscopic suturing device according to the embodiment of the present invention.
Figure 9:
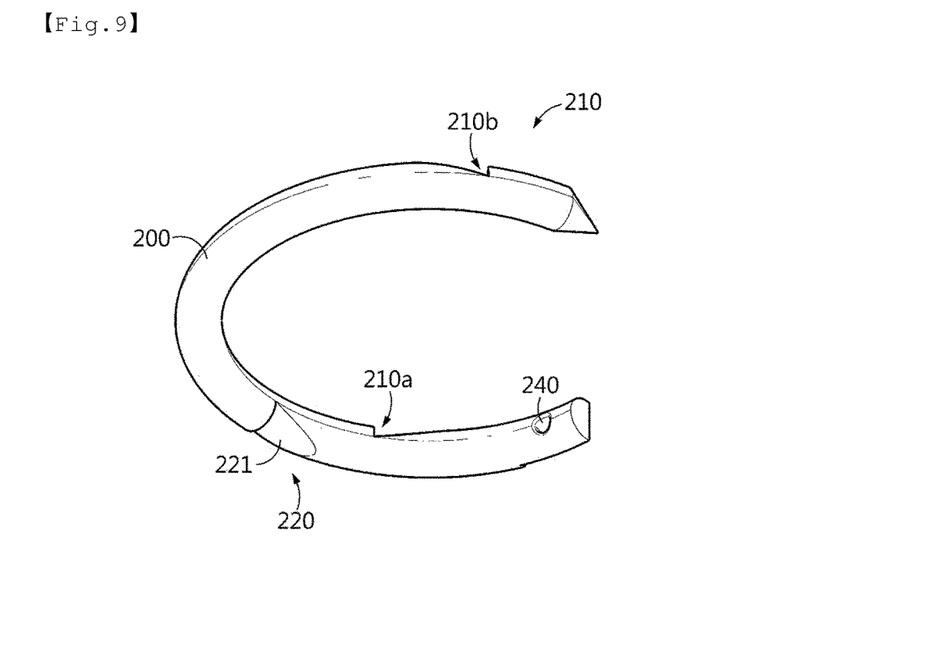
FIG. 9 is a perspective view of a lower side of the curved needle in the endoscopic suturing device according to the embodiment of the present invention.
Figure 10:
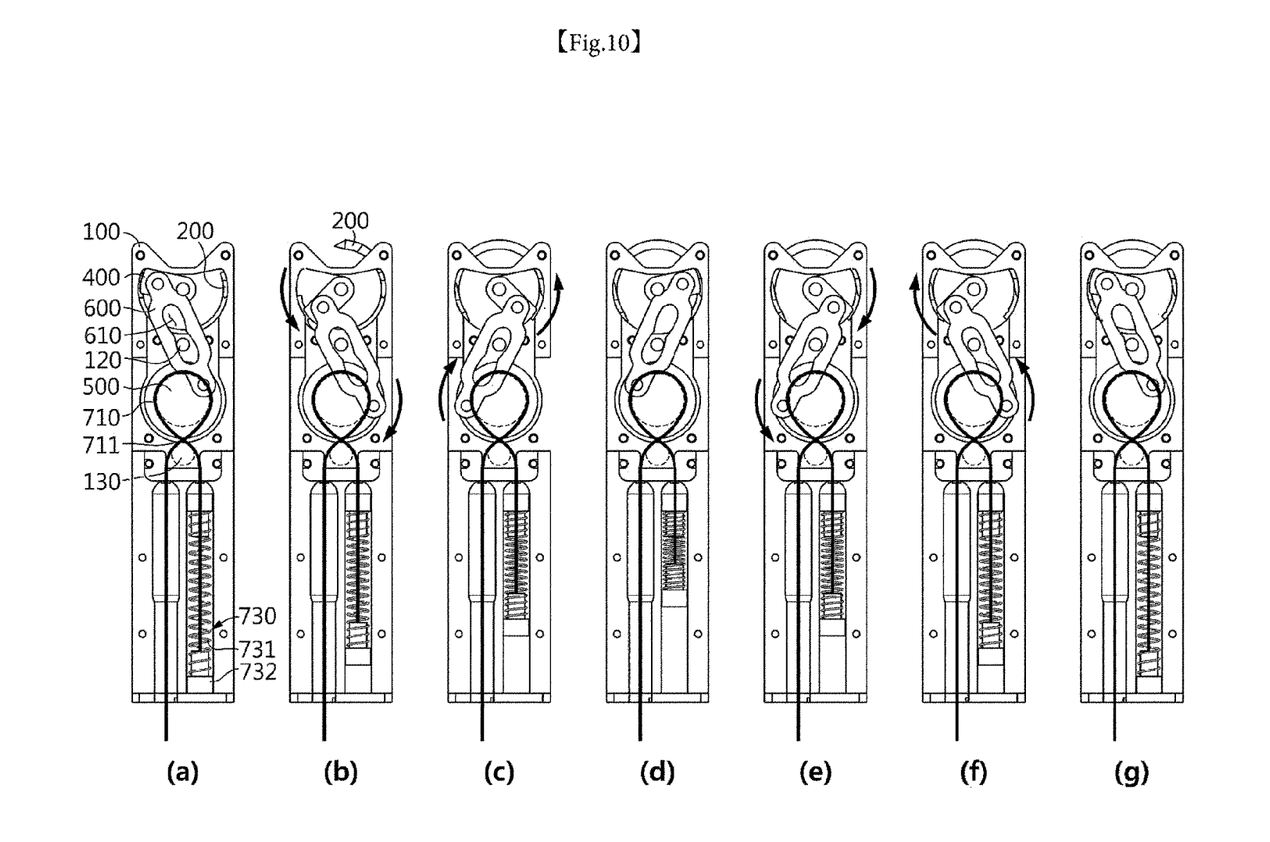
FIG. 10 is a view showing the operation of the endoscopic suturing device according to the embodiment of the present invention.

FIG. 1 is a perspective view of an endoscopic suturing device according to an embodiment of the present invention to which an endoscope is coupled, FIG. 2 is a partial exploded view of the endoscopic suturing device according to the embodiment of the present invention, FIGS. 3 and 4 are sectional views illustrating the principle by which the endoscopic suturing device according to the embodiment of the present invention is operated, FIG. 5 is a view showing a connection link in the endoscopic suturing device according to the embodiment of the present invention, FIG. 6 is a perspective view showing the state in which a needle driver and a needle stopper are in contact with a curved needle in the endoscopic suturing device according to the embodiment of the present invention, FIG. 7 is a perspective view showing the state in which the needle driver and the needle stopper are separated from the curved needle of FIG. 6, FIG. 8 is a perspective view of an upper side of the curved needle in the endoscopic suturing device according to the embodiment of the present invention, FIG. 9 is a perspective view of a lower side of the curved needle in the endoscopic suturing device according to the embodiment of the present invention, and FIG. 10 is a view showing the operation of the endoscopic suturing device according to the embodiment of the present invention.

Referring to FIGS. 1 to 10, the endoscopic suturing device 10 according to the embodiment of the present invention includes a body member 100, a curved needle 200, a needle driver 300, a driven link 400, a driving link 500, a connection link 600, and a power supply source 700.

The curved needle 200, the needle driver 300, the driven link 400, the driving link 500, the connection link 600, and an elastic member of the power supply source 700 are seated on the body member 100. The body member 100 is provided with a coupling portion 110, to which an endoscope 900 is coupled. Referring to FIG. 1, the endoscope 900 is coupled to the coupling portion 110 of the body member 100 such that the body member 100 is moved together with the endoscope 900. The body member 100 may be provided with a projecting portion 120 and a wire supporting portion 130, a description of which will follow.

Referring to FIG. 8, a suture 230 is coupled to the curved needle 200. Referring to FIGS. 3 and 4, the curved needle 200 is rotatably seated on the body member 100. To this end, the body member 100 may be provided with a needle seating portion 140 having a shape corresponding to the shape of the curved needle 200, and the curved needle 200 is seated on the needle seating portion 140 so as to be guided during rotation.

Referring to FIG. 9, the curved needle 200 may be provided with a suture coupling hole 240 configured to allow the suture 230 to be coupled thereto, and the suture 230 is coupled to the suture coupling hole 240 so as to be movable together with the curved needle 200.

The curved needle 200 may be configured to be rotated by the needle driver 300. Referring to FIG. 6, when the needle driver 300 is rotated in contact with the curved needle 200, the curved needle 200 is rotated together with the needle driver 300 by pressing force from the needle driver 300. To this end, the curved needle 200 may be provided with driver recesses 210a and 210b configured to allow the needle driver 300 to be brought into contact therewith.

Rotation of the curved needle 200 in a direction opposite a predetermined rotation direction thereof may be prevented by a needle stopper 800. To this end, referring to FIGS. 7 and 9, the curved needle 200 may be provided with a stopper recess 220 configured to allow projecting portions 820a and 820b of the needle stopper 800 to be brought into contact therewith. A detailed description thereof will be given below.

Referring to FIGS. 6 and 7, the needle driver 300 is coupled to the driven link 400 so as to be rotatable together with the driven link 400, and is brought into contact with the driver recesses 210a and 210b of the curved needle 200 to rotate the curved needle 200 while pressing the curved needle 200.

The needle driver 300 is formed so as to project from the driven link 400 toward the curved needle 200 side. Here, the needle driver 300 may be disposed at an upper side or a lower side of the curved needle 200. Hereinafter, however, a description will be given based on the case in which the needle driver 300 is disposed at the upper side of the curved needle 200 for convenience of description.

That is, the needle driver 300 projects on the driven link 400 from the upper side of the curved needle 200 to a lower side at which the curved needle 200 is disposed. The needle driver 300 is brought into contact with the driver recesses 210a and 210b formed in the curved needle 200, and the needle driver 300 presses the curved needle 200 so as to be rotated. Here, the driver recesses 210a and 210b may be formed in an upper side of the curved needle 200, as shown in FIGS. 7 and 8; however, the present invention is not limited thereto.

The needle driver 300 may be formed so as to be gradually inclined from the front to the rear in an advance direction of the needle driver 300 (direction indicated by arrow X in FIG. 7). Here, the needle driver 300 may include a first straight portion 310, a second straight portion 320, and a first inclined portion 330.

The first straight portion 310 projects in a straight line from the front of the driven link 400 in the advance direction of the needle driver 300. For example, the first straight portion 310 projects downwards from the driven link 400 at the front of the driven link 400.

The second straight portion 320 projects in a straight line from the rear of the driven link 400 in the advance direction of the needle driver 300. For example, the second straight portion 320 projects downwards from the driven link 400 at the rear of the driven link 400.

The second straight portion 320 is configured to have a smaller length than the first straight portion 310. When there is a difference in length between the first straight portion 310 and the second straight portion 320, as described above, an inclination may be formed between the first straight portion 310 and the second straight portion 320.

Here, the first inclined portion 330 is configured to connect the first straight portion 310 and the second straight portion 320 to each other in an inclined state. Meanwhile, a second inclined portion 211 corresponding to the first inclined portion 330 of the needle driver 300 may be formed in each of the driver recesses 210a and 210b formed in the curved needle 200. When the first inclined portion 330 is brought into contact with the second inclined portion 211, the needle driver 300 may be seated in the driver recess 210a of the curved needle 200, as shown in FIG. 6.

When the driven link 400 is rotated, the needle driver 300 is also rotated therewith, and the first straight portion 310 of the needle driver 300 presses the driver recess 210a formed in the curved needle 200. When the curved needle 200 is pressed by the needle driver 300, the curved needle 200 is rotated in the same direction as the rotating direction of the needle driver 300.

The needle driver 300 is rotated in a predetermined direction by a predetermined angle, e.g. 180° (hereinafter, rotation in the predetermined direction will be referred to as forward rotation), and is then reversely rotated in a direction opposite the forward rotation direction, whereby the needle driver returns to the original position thereof.

The needle driver 300 may be made of an elastic material such that the needle driver 300 can be easily separated from the driver recess 210 of the curved needle 200 during reverse rotation of the needle driver 300.

Meanwhile, although the predetermined angle is not limited to 180°, a description will be given hereinafter based on the case in which the needle driver 300 is rotated once by 180° for convenience of description.

After being forwardly rotated in the predetermined direction by the predetermined angle, e.g. 180°, the needle driver is rotated in a reverse direction by 180°, whereby the needle driver returns to the original position thereof. When the needle driver 300 is forwardly rotated twice in the predetermined direction by 180°, as described above, the curved needle 200 is forwardly rotated by 360°. That is, when the needle driver 300 is forwardly rotated once by 180°, is reversely rotated by 180°, and is forwardly rotated by 180°, i.e. when the needle driver is forwardly rotated twice, the curved needle 200 is forwardly rotated by 360°.

Meanwhile, when the needle driver 300 is reversely rotated to return to the original position thereof, the curved needle 200 is also reversely rotated. However, the curved needle 200 is repeatedly forwardly and reversely rotated, whereby the curved needle is not forwardly rotated by 360°.

When the needle driver 300 is reversely rotated to return to the original position thereof, therefore, the curved needle 200 must not be rotated but stopped. To this end, the needle stopper 800 is brought into contact with the curved needle 200 to prevent reverse rotation of the curved needle 200.

That is, when the needle driver 300 is forwardly rotated, the curved needle 200 is also forwardly rotated together with the needle driver 300. When the needle driver 300 is reversely rotated, however, the curved needle 200 is stopped by the needle stopper 800.

When the needle driver 300 is repeatedly forwardly and reversely rotated by 180°, therefore, the curved needle 200 is repeatedly forwardly rotated by 180° and stopped. That is, when the needle driver 300 is repeatedly forwardly and reversely rotated by 180°, the curved needle 200 is continuously rotated in the forward rotation direction. The operation of the needle stopper 800 will be described in detail below.

Meanwhile, as previously described, the needle driver 300 is forwardly rotated twice by 180° to forwardly rotate the curved needle 200 by 360°. To this end, as shown in FIG. 6, the curved needle 200 is provided with a pair of driver recesses 210a and 210b.

When describing this, the needle driver 300 is coupled to the driver recess 210a and forwardly rotates the curved needle 200 once by 180°. When the needle driver 300 is reversely rotated by 180° to return to the original position thereof, the needle driver 300 may be seated in the driver recess 210b, and the needle driver 300 is coupled to the driver recess 210b and forwardly rotates the curved needle 200 once again by 180°.

Since the curved needle 200 is forwardly rotated twice by 180°, the curved needle is forwardly rotated by 360°, i.e. one turn of the curved needle in the forward direction is achieved. Here, the pair of driver recesses 210a and 210b is formed in the curved needle 200 at positions at which the driver recesses face each other, and the second inclined portions 211 of the pair of driver recesses 210a and 210b are formed so as to be inclined in opposite directions, as shown in FIGS. 7 and 8.

Referring to FIGS. 2, 3, and 4, the driven link 400 is rotatably seated on the body member 100. The driven link 400 is connected to the driving link 500 via the connection link 600, and rotational force of the driving link 500 is transmitted to the drive link 400 via the connection link 600, whereby the driven link 400 is rotated.

The driven link 400 may be rotated in a clockwise direction and a counterclockwise direction. The clockwise direction may be the forward rotation direction of the driven link 400, or the counterclockwise direction may be the forward rotation direction of the driven link 400. Hereinafter, however, a description will be given based on the case in which the counterclockwise direction rotation of the driven link 400 is set to forward rotation for convenience of description.

In this case, a description will be given based on the case in which the counterclockwise direction rotation of each of the needle driver 300, coupled to the driven link 400 so as to be rotated together with the driven link 400, and the curved needle 200, pressed by the needle driver 300 so as to be rotated in the same direction as the needle driver 300, is also set to forward rotation.

The driven link 400 is configured to be repeatedly forwardly and reversely rotated by rotation of the driving link 500.

Referring to FIGS. 2, 3, and 4, the driving link 500 is seated on the body member 100, and is spaced apart from the driven link 400 so as to be rotatable. The driving link 500 is connected to the driven link 400 via the connection link 600, and rotational force of the driving link 500 is transmitted to the drive link 400 via the connection link 600.

The driving link 500 receives power from the power supply source 700. The driving link 500 may be rotated in the clockwise direction and the counterclockwise direction. The clockwise direction may be the forward rotation direction of the driving link 500, or the counterclockwise direction may be the forward rotation direction of the driving link 500. Hereinafter, however, a description will be given based on the case in which the clockwise direction rotation of the driving link 500 is set to forward rotation for convenience of description.

The driving link 500 is configured to be repeatedly forwardly and reversely rotated by power from the power supply source 700.

Here, the driving link 500 and the driven link 400 are rotated in opposite directions based on forward rotation. For example, when the driving link 500 is forwardly rotated in the clockwise direction, the driven link 400 is forwardly rotated in the counterclockwise direction.

Referring to FIGS. 2, 3, and 4, the connection link 600 connects the driving link 500 and the driven link 400 to each other and transmits rotational force of the driving link 500 to the driven link 400. As previously described, the connection link 600 may be fitted onto the projecting portion 120 formed on the body member 100 so as to be coupled thereto.

Referring to FIG. 5, the connection link 600 may be provided with a through-hole 610 such that the connection link 600 is fitted onto the projecting portion 120. Referring to FIGS. 3 and 4, the projecting portion 120 may be inserted through the through-hole 610 of the connection link 600, and the connection link 600 may be moved in the state in which at least a part of an inner circumference of the through-hole 610 is in contact with the projecting portion 120.

That is, the connection link 600 is moved while the through-hole 610 of the connection link 600 is guided by the projecting portion 120. Here, referring to FIG. 5, the through-hole 610 may be configured such that the width of the through-hole is gradually changed from a central part 511 to opposite ends thereof.

In addition, the shape of the through-hole 610 from the central part 611 to one end thereof, i.e. a first end 612, and the shape of the through-hole 610 from the central part 611 to the other end thereof, i.e. a second end 613, may be symmetrical to each other.

For example, the through-hole 610 may be formed such that the width of the through-hole is increased from the central part 611 to a predetermined first part 614 extending toward the first end 612 and the width of the through-hole is decreased from the first part 614 to the first end 612. In addition, the through-hole 610 may be formed such that the width of the through-hole is increased from the central part 611 to a predetermined second part 615 extending toward the second end 613 and the width of the through-hole is decreased from the second part 615 to the second end 613.

Here, the through-hole 610 may be formed so as to have a straight shape or a curved shape. Hereinafter, however, a description will be given base on the case in which the through-hole 610 is formed so as to have a curved shape for convenience of description.

When the through-hole 610 has the above shaped, i.e. when the width of the through-hole 610 is gradually changed from the central part 611 to each end thereof and the overall shape of the through-hole 610 is curved, it is possible to solve a change point problem in that the driven link 400 forwardly rotated in the counterclockwise direction according to the forward rotation of the driving link 500 when the driving link 500 is forwardly rotated in the clockwise direction is rotated in the clockwise direction, which is a reverse direction, at a certain position, e.g. the lowest point of a rotational circumference of the driven link 400, whereby the driven link returns to the original position thereof. A description will be given hereinafter in connection with the change point problem.

MODE FOR INVENTION

Figure 11:
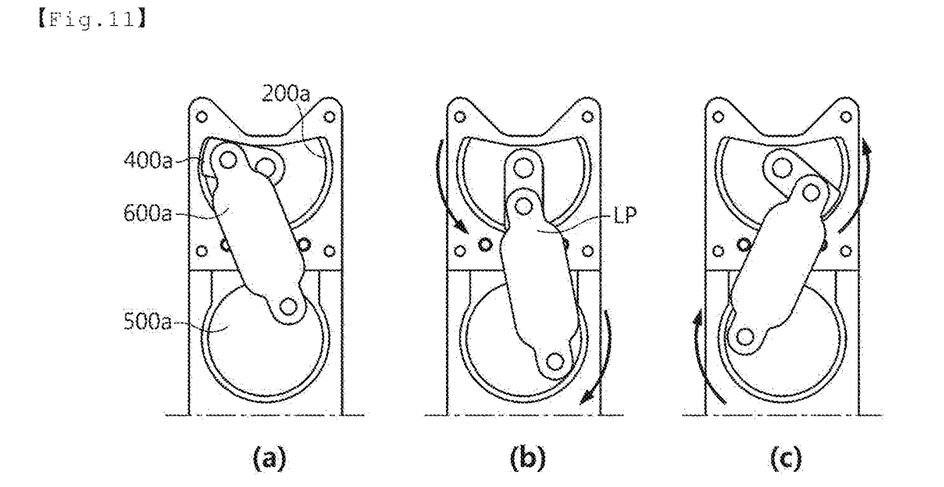
FIG. 11 is a view showing a normal operation when no through-hole is formed in the connection link provided in the endoscopic suturing device.
Figure 12:
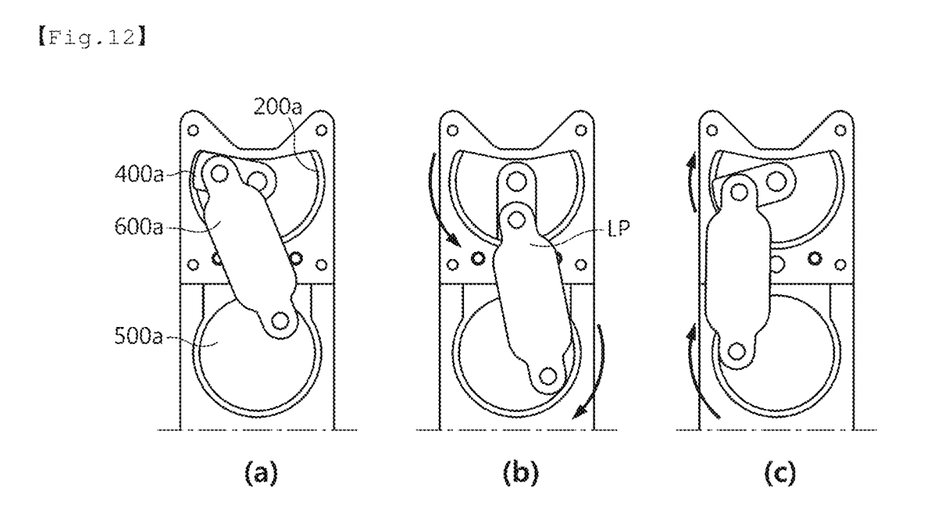
FIG. 12 is a view showing an abnormal operation when no through-hole is formed in the connection link provided in the endoscopic suturing device.

FIG. 11 is a view showing a normal operation when no through-hole is formed in the connection link provided in the endoscopic suturing device, and FIG. 12 is a view showing an abnormal operation when no through-hole is formed in the connection link provided in the endoscopic suturing device.

In connection with the change point problem, a description will be given in detail with reference to FIGS. 11 and 12, in each of which no through-hole 610 is formed in a connection link 600a, by way of example.

Referring to FIGS. 11 and 12, when a driving link 500a is rotated from the position of each of FIGS. 11(a) and 12(a) in the clockwise direction, a driven link 400a is rotated in the counterclockwise direction and reaches the lowest point LP of a rotational circumference of the driven link 400a, as shown in each of FIGS. 11(b) and 12(b).

When the driving link 500a is further rotated in the clockwise direction in the state in which the connection link 600a reaches the lowest point LP of the rotational circumference of the driven link 400a, the driven link 400a and the connection link 600a may be normally rotated in the counterclockwise direction, as shown in FIG. 11(c), or may be abnormally reversely rotated in the clockwise direction to return to the original positions thereof, as shown in FIG. 12(c).

That is, as shown in FIG. 12(c), the driven link 400a is not rotated any more in the forward rotation direction and returns to the original position thereof due to reverse rotation thereof at the lowest point LP of the rotational circumference of the driven link, i.e. a change point. When the driven link 400a is not rotated any more in the forward rotation direction and returns to the original position thereof, as described above, a curved needle 200a is also not normally rotated, whereby it is not possible to perform accurate suturing.

In order to solve this problem, the endoscopic suturing device 10 according to the embodiment of the present invention may be configured such that the through-hole 610 has the above structure. In the case in which the through-hole 610 has the above structure, when the driving link 400 reaches the lowest point of the rotational circumference of the driven link 400, i.e. the change point, the projecting portion 120 of the body member 100 is located at the end of the through-hole 610 having a width greater than the width of the central part 611 of the through-hole 610, whereby the connection link 600 is accurately rotated in the forward direction while the inner circumference of the through-hole 610 is guided along the projecting portion 120 by the projecting portion 120 through a margin space between the widths of the through-hole 610 without being constrained by the projecting portion 120, and the driven link 400 connected to the connection link 600 is also rotated in the forward direction.

That is, in the embodiment of the present invention, the width of the through-hole 610 is changed, whereby the through-hole 610 is not constrained by the projecting portion 120 of the body member 100, and therefore smooth rotation is achieved.

The power supply source 700 is coupled to the driving link 500 to provide rotational force to the driving link 500. Referring to FIGS. 3 and 4, the power supply source 700 may include a wire 710, a handle 720, and an elastic member 730.

The wire 710 is wound around the driving link 500, and has two ends. That is, opposite ends of the wire 710 are separated from each other. As shown in FIGS. 3 and 4, the wire 710 is wound around the driving link 500, and is configured to have an intersection 711 that intersects between a wire supporting portion 130 formed at the body member 100 and the driving link 500. That is, one end of the wire 710 is withdrawn outwards from the body member 100 and is coupled to the handle 720 in the state in which the wire is wound around the driving link 500 and is twisted once. The other end of the wire 710 is connected to the elastic member 730, which is installed inside the body member 100. The wire 710 is brought into contact with the wire supporting portion 130 so as to be supported by the wire supporting portion 130 at the position adjacent to the intersection 711 of the wire 710.

The handle 720 is coupled to one end of the wire 710 so as to pull the wire 710. For example, the handle 720 may be coupled to the wire 710 on the left side of the wire 710 based on FIGS. 3 and 4.

The handle 720 may be variously configured. For example, as shown in FIGS. 3 and 4, the handle may be manufactured so as to have a gun-like shape. That is, when a trigger of the gun is pushed, the wire 710 is pulled, and when the trigger of the gun is released, the wire 710 returns to the original position thereof due to elastic restoring force.

However, the shape of the handle 720 is not limited to the gun, and the handle may have various shapes. In addition, although the handle 720 is shown as being manually manipulated by a user in FIGS. 3 and 4, a controller may be installed such that pulling and releasing of the wire 710 are automatically controlled.

The elastic member 730 is connected to the other end of the wire 710 to provide elastic force to the wire 710. For example, the elastic member 730 may be connected to the wire 710 on the right side of the wire 710 based on FIGS. 3 and 4.

The elastic member 730 may include a spring 731 and a compression portion 732. Various types of springs may be used as the spring 731. For example, a coil spring may be used. When the spring 731 is a coil spring, the wire 710 may be disposed inside the spring 731. That is, the wire 710 may be coupled to the compression portion 732 via the inside of the spring 731.

The compression portion 732 is coupled to the end of the spring 731 and is also coupled to the wire 710. When the wire 710 is pulled, the spring 731 is compressed. That is, when the wire 710 is pulled through the handle 720, as shown in FIG. 3, the compression portion 732 presses the spring 731 to elastically contract the spring, as shown in FIG. 4. When the power pulling the wire 710 is removed and thus pulling of the wire 710 is released, the spring 731 is elastically expanded by elastic restoring force of the spring 731, as shown in FIG. 3.

That is, when the wire 710 is pulled by operation of the handle 720, as shown in FIG. 3, the driving link 500 is rotated in the forward direction, i.e. the clockwise direction, the elastic member 730 is elastically contracted, and the driven link 400 is rotated in the forward direction, i.e. the counterclockwise direction, as shown in FIG. 4. When the driven link 400 is rotated, as described above, the needle driver 300 and the curved needle 200 are also forwardly rotated in the counterclockwise direction.

When the power pulling the wire 710 is removed, the elastic member 730 is elastically expanded by elastic restoring force of the elastic member 730, and the driving link 500 is rotated in a direction opposite the rotation direction when the wire 710 is pulled, i.e. the reverse direction, which is the counterclockwise direction, as shown in FIG. 3. In addition, the driven link 400 is rotated in the reverse direction, i.e. the clockwise direction. Even though the driven link 400 is reversely rotated, the curved needle 200 is stopped by the needle stopper 800.

The needle stopper 800 is configured to prevent reverse rotation of the curved needle 200 when the needle driver 300 is reversely rotated due to reverse rotation of the driven link 400. That is, the needle stopper 800 may be disposed at a position opposite the needle driver 300 so as to be brought into contact with the curved needle 200 in order to stop the curved needle 200 when the needle driver 300 is reversely rotated.

For example, when the needle driver 300 is disposed at the upper side of the curved needle 200, as shown in FIG. 6, the needle stopper 800 is disposed at the lower side of the curved needle 200.

However, when the needle driver 300 is forwardly rotated, i.e. when the curved needle 200 is forwardly rotated, the needle stopper 800 must not disturb rotation of the curved needle 200. Consequently, a projecting portion 820 of the needle stopper 800 may be made of an elastic material such that the projecting portion 820 can be easily separated from the stopper recess 220 of the curved needle 200 when the curved needle 200 is forwardly rotated.

Referring to FIG. 7, the needle stopper 800 may include a supporting rod 810 and a pair of projecting portions 820a and 820b.

The supporting rod 810 may be a longitudinal member, e.g. a straight member, and is coupled to the body member 100 in various manners.

The projecting portion 820 may be configured to project from the supporting rod 810 toward the curved needle 200 side. In addition, as previously described, the stopper recess 220 may be formed in the curved needle 200, and the projecting portion 820 of the needle stopper 800 may be brought into contact with the stopper recess 220. Here, the stopper recess 220 may be formed at the lower side of the curved needle 200, as shown in FIGS. 7 and 9; however, the present invention is not limited thereto.

The projecting portion 820 may be formed so as to be gradually inclined from the front to the rear in an advance direction of the curved needle 200 (direction indicated by arrow X in FIG. 7). To this end, referring to FIG. 7, the projecting portion 820 may include a third straight portion 821, a fourth straight portion 822, and a third inclined portion 823.

The third straight portion 821 projects in a straight line from the front of the supporting rod 810 in the advance direction of the curved needle 200. For example, the third straight portion 821 projects upwards from the supporting rod 810 at the front of the supporting rod 810.

The fourth straight portion 822 projects in a straight line from the rear of the supporting rod 810 in the advance direction of the curved needle 200. For example, the fourth straight portion 822 projects upwards from the supporting rod 810 at the rear of the supporting rod 810.

The fourth straight portion 822 is configured to have a smaller length than the third straight portion 821. When there is a difference in length between the third straight portion 821 and the fourth straight portion 822, as described above, an inclination may be formed between the third straight portion 821 and the fourth straight portion 822.

Here, the third inclined portion 823 is configured to connect the third straight portion 821 and the fourth straight portion 822 to each other in an inclined state.

Meanwhile, a fourth inclined portion 221 (see FIG. 9) corresponding to the third inclined portion 823 of the projecting portion 820 may be formed in the stopper recess 220 formed in the curved needle 200. When the third inclined portion 823 is brought into contact with the fourth inclined portion 221, the projecting portion 820 of the needle stopper 800 may be seated in the stopper recess 220 of the curved needle 200.

As previously described, the needle driver 300 is rotated in the predetermined direction by the predetermined angle, e.g. 180°, and is then reversely rotated in the direction opposite the forward rotation direction, whereby the needle driver returns to the original position thereof.

When the needle driver 300 is reversely rotated to return to the original position thereof, the curved needle 200 is also reversely rotated. However, the curved needle 200 is repeatedly forwardly and reversely rotated, whereby the curved needle is not forwardly rotated by 360°.

When the needle driver 300 is reversely rotated to return to the original position thereof, therefore, the curved needle 200 must not be rotated but stopped. As shown in FIG. 6, the projecting portion 820 of the needle stopper 800 is brought into contact with the stopper recess 220 of the curved needle 200 to prevent reverse rotation of the curved needle 200.

That is, when the needle driver 300 is also reversely rotated according to reverse rotation of the driven link 400, the stopper recess 220 of the curved needle 200 is caught by the third straight portion 821 of the projecting portion 820, whereby reverse rotation of the curved needle 200 is prevented.

Meanwhile, referring to FIG. 7, the pair of projecting portions 820a and 820b may be disposed at opposite positions, and the third inclined portions 823 of the pair of projecting portions 820a and 820b may be formed so as to be inclined in opposite directions. The reason for this is that the curved needle 200 is rotated by 180°. That is, when the curved needle 200 is forwardly rotated by 180° in a state of being caught by the projecting portion 820a, the curved needle is caught by the projecting portion 820b. When the curved needle 200 is forwardly rotated again by 180°, the curved needle is caught again by the projecting portion 820a.

Hereinafter, the operation and effects of the endoscopic suturing device 10 according to the embodiment of the present invention will be described with reference to the drawings.

Referring to FIG. 10(a), the wire 710 is not pulled, the spring 731 is expanded, and the driving link 500, the connection line 600, and the driven link 400 are all stopped.

When the wire 710 is pulled by the handle 720 in the state of FIG. 10(a), as shown in FIG. 10(b), the driving link 500, around which the wire 710 is wound, is forwardly rotated in a direction indicated by an arrow, i.e. the clockwise direction, and the driven link 400 is forwardly rotated in the direction indicated by the arrow, i.e. the counterclockwise direction. The curved needle 200 is rotated in the counterclockwise direction together with the driven link 400 by the needle driver 300. The connection link 600 is moved in a state of being connected to the driving link 500 and the driven link 400. The spring 731 is compressed by the compression portion 732.

When the wire 710 is continuously pulled, the driven link 400 is continuously moved in the counterclockwise direction, as shown in FIG. 10(c). That is, since the width of the through-hole 610 is gradually changed toward opposite ends thereof, the through-hole 610 is not constrained by the projecting portion 120, and therefore the driven link 400 may be smoothly moved in the counterclockwise direction.

When the driven link 400 is continuously moved in the counterclockwise direction and reaches the position of FIG. 10(d), the curved needle 200 is rotated by 180°. At this time, the spring 731 is maximally compressed.

When pulling of the wire 710 is released by the handle 720, the spring 731 is expanded by elastic restoring force of the spring 731, and the wire 710 is moved in a direction opposite the direction in which the wire has been pulled, and the driving link 500 is reversely rotated in a direction indicated by an arrow, i.e. in the counterclockwise direction, and the driven link 400 is reversely rotated in the direction indicated by the arrow, i.e. in the clockwise direction, as shown in FIG. 10(e). At this time, the curved needle 200 is stopped by the needle stopper 800. The connection link 600 is moved in a state of being connected to the driving link 500 and the driven link 400.

After returning to FIG. 10(g) via FIG. 10(f), the processes after FIG. 10(b) are repeated to rotate the curved needle 200.

Although the present invention has been described with reference to the limited embodiments and the drawings, the present invention is not limited thereto, and various modifications and alternations are possible by those skilled in the art to which the present invention pertains within the technical idea of the present invention and an equivalent range of the appended claims.

DESCRIPTION OF REFERENCE NUMERALS

10: Endoscopic suturing device 100: Body member
110: Coupling portion 120: Projecting portion
130: Wire supporting portion 140: Needle seating portion
200: Curved needle 210: Driver recess
211: Second inclined portion 220: Stopper recess
230: Suture 240: Suture coupling hole
221: Fourth inclined portion 300: Needle driver
310: First straight portion 320: Second straight portion
330: First inclined portion 400: Driven link
500: Driving link 600: Connection link
610: Through-hole 611: Central part
612: First end 613: Second end
614: First part 615: Second part
700: Power supply source 710: Wire
711: Intersection 720: Handle
730: Elastic member 731: Spring
732: Compression portion 800: Needle stopper
810: Supporting rod 820: Projecting portion
821: Third straight portion 822: Fourth straight portion
823: Third inclined portion 900: Endoscope

INDUSTRIAL APPLICABILITY

When an endoscopic suturing device according to the present invention is used, it is possible to perform suturing with high reliability irrespective of a suture range, and therefore the present invention can be usefully used for simple suturing procedures and various internal surgeries such as gastrointestinal reduction surgery and NOTES, which uses a natural opening.

The invention claimed is:

1. An endoscopic suturing device comprising:
   a body member having formed thereon a coupler configured to allow an endoscope to be coupled thereto;
   a curved needle configured to allow a suture to be coupled thereto, the curved needle being rotatably seated on the body member;
   a needle driver brought into contact with the curved needle, the needle driver being configured to rotate the curved needle;
   a driven link configured to allow the needle driver to be coupled thereto, the driven link being configured to be rotatable;
   a driving link spaced apart from the driven link, the driving link being configured to be rotatable;
   a connection link configured to connect the driving link and the driven link to each other and to transmit rotational force of the driving link to the driven link; and
   a power supply source coupled to the driving link, the power supply source being configured to provide rotational force to the driving link,
   wherein the body member is provided with a projecting portion, the connection link is provided with a through-hole, and the projecting portion is inserted through the through-hole of the connection link and the connection link is moved in a state in which at least a part of an inner circumference of the through-hole is in contact with the projecting portion,
   wherein the through-hole is configured such that a width of the through-hole is gradually changed from a central part to opposite ends thereof,
   wherein the through-hole is configured such that a shape of the through-hole from the central part to a first end, which is one end, and a shape of the through-hole from the central part to a second end, which is the other end, are symmetrical to each other, and
   wherein the through-hole is formed such that a width of the through-hole is increased from the central part to a predetermined first part extending toward the first end and a width of the through-hole is decreased from the first part to the first end.

2. The endoscopic suturing device according to claim 1, wherein the through-hole is formed such that a width of the through-hole is increased from the central part to a predetermined second part extending toward the second end and a width of the through-hole is decreased from the second part to the second end.

3. The endoscopic suturing device according to claim 1, wherein
the power supply source comprises:
a wire wound around the driving link, the wire having two ends;
a handle coupled to one of the ends of the wire, the handle being configured to pull the wire; and
an elastic member connected to the other of the ends of the wire, the elastic member being configured to provide elastic force to the wire,
the body member is provided with a wire supporting portion configured to support the wire, and
the wire is wound around the driving link, the wire being configured to have an intersection that intersects between the driving link and the wire supporting portion.

4. The endoscopic suturing device according to claim 3, wherein
when the wire is pulled by operation of the handle, the driving link is rotated in any one of a clockwise direction and a counterclockwise direction, whereby the elastic member is elastically contracted, and
when power pulling the wire is removed, the elastic member is elastically expanded by elastic restoring force of the elastic member, whereby the driving link is rotated in a direction opposite the rotation direction when the wire is pulled.

5. The endoscopic suturing device according to claim 4, wherein the elastic member comprises:
a spring configured to allow the wire to be disposed therein; and
a compression portion coupled to an end of the spring and to the wire, the compression portion being configured to compress the spring when the wire is pulled.

6. The endoscopic suturing device according to claim 1, wherein
the needle driver is coupled to the driven link, the needle driver being formed so as to project from the driven link to the curved needle, and
the curved needle is provided with a driver recess configured to allow the needle driver to be brought into contact therewith.

7. The endoscopic suturing device according to claim 6, wherein the needle driver is formed so as to be gradually inclined from a front to a rear in an advance direction of the needle driver.

8. The endoscopic suturing device according to claim 7, wherein the needle driver comprises:
a first straight portion projecting in a straight line from a front of the driven link in the advance direction of the needle driver;
a second straight portion projecting in a straight line from a rear of the driven link in the advance direction of the needle driver, the second straight portion having a smaller length than the first straight portion; and
a first inclined portion configured to connect the first straight portion and the second straight portion to each other in an inclined state.

9. The endoscopic suturing device according to claim 8, wherein the driver recess is provided with a second inclined portion corresponding to the first inclined portion of the needle driver such that the needle driver is seated in the driver recess.

10. The endoscopic suturing device according to claim 9, wherein
the driver recess is provided in a pair,
the pair of driver recesses is formed in the curved needle at positions at which the driver recesses face each other, and
the second inclined portions of the pair of driver recesses are formed so as to be inclined in opposite directions.

11. The endoscopic suturing device according to claim 1, further comprising a needle stopper disposed at a position opposite the needle driver, the needle stopper being brought into contact with the curved needle to stop the curved needle.

12. The endoscopic suturing device according to claim 11, wherein
the needle stopper comprises:
a supporting rod coupled to the body member; and
a pair of projecting portions projecting from the supporting rod to the curved needle, and
the curved needle is provided with a stopper recess configured to allow the projecting portions to be brought into contact therewith.

13. The endoscopic suturing device according to claim 12, wherein each of the projecting portions is formed so as to be gradually inclined from a front to a rear in an advance direction of the curved needle.

14. The endoscopic suturing device according to claim 13, wherein each of the projecting portions comprises:
a third straight portion projecting in a straight line from a front of the supporting rod in the advance direction of the curved needle;
a fourth straight portion projecting in a straight line from a rear of the supporting rod in the advance direction of the curved needle, the fourth straight portion having a smaller length than the third straight portion; and
a third inclined portion configured to connect the third straight portion and the fourth straight portion to each other in an inclined state.

15. The endoscopic suturing device according to claim 14, wherein the stopper recess is provided with a fourth inclined portion corresponding to the third inclined portion of each of the projecting portions such that each of the projecting portions of the needle stopper is seated in the stopper recess.

16. The endoscopic suturing device according to claim 15, wherein
the pair of projecting portions is disposed at opposite positions, and
the third inclined portions of the pair of projecting portions are formed so as to be inclined in opposite directions.

17. An endoscopic suturing device comprising:
a body member having formed thereon a coupler configured to allow an endoscope to be coupled thereto;
a curved needle configured to allow a suture to be coupled thereto, the curved needle being rotatably seated on the body member;
a needle driver brought into contact with the curved needle, the needle driver being configured to rotate the curved needle;
a driven link configured to allow the needle driver to be coupled thereto, the driven link being configured to be rotatable;
a driving link spaced apart from the driven link, the driving link being configured to be rotatable;
a connection link configured to connect the driving link and the driven link to each other and to transmit rotational force of the driving link to the driven link;

a power supply source coupled to the driving link, the power supply source being configured to provide rotational force to the driving link; and a needle stopper disposed at a position opposite the needle driver, the needle stopper being brought into contact with the curved needle to stop the curved needle, wherein the needle stopper comprises: a supporting rod coupled to the body member; and a pair of projecting portions projecting from the supporting rod to the curved needle, and the curved needle is provided with a stopper recess configured to allow the projecting portions to be brought into contact therewith, wherein each of the projecting portions is formed so as to be gradually inclined from a front to a rear in an advance direction of the curved needle, and wherein each of the projecting portions comprises: a third straight portion projecting in a straight line from a front of the supporting rod in the advance direction of the curved needle; a fourth straight portion projecting in a straight line from a rear of the supporting rod in the advance direction of the curved needle, the fourth straight portion having a smaller length than the third straight portion; and a third inclined portion configured to connect the third straight portion and the fourth straight portion to each other in an inclined state.

18. The endoscopic suturing device according to claim 17, wherein the stopper recess is provided with a fourth inclined portion corresponding to the third inclined portion of each of the projecting portions such that each of the projecting portions of the needle stopper is seated in the stopper recess.

19. The endoscopic suturing device according to claim 18, wherein the pair of projecting portions is disposed at opposite positions, and the third inclined portions of the pair of projecting portions are formed so as to be inclined in opposite directions.

* * * * *